United States Patent
Glazier et al.

(10) Patent No.: US 7,001,396 B2
(45) Date of Patent: *Feb. 21, 2006

(54) SAFETY INTRODUCER ASSEMBLY AND METHOD

(75) Inventors: Valerie Glazier, Minnetonka, MN (US); Todd Latterell, Crystal, MN (US)

(73) Assignee: Enpath Medical, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 188 days.

(21) Appl. No.: 10/403,265

(22) Filed: Mar. 26, 2003

(65) Prior Publication Data

US 2004/0193112 A1    Sep. 30, 2004

(51) Int. Cl.
*A61F 11/00* (2006.01)

(52) U.S. Cl. ............ 606/108; 606/167; 606/182; 606/185; 604/500; 604/164.1; 604/164.12; 604/164.03; 604/264

(58) Field of Classification Search ............ 604/23, 604/26, 44, 500, 506–508, 117, 110, 158, 604/161–163, 164.01, 164.05–164.12, 170.01, 604/170.02, 264, 263, 164.03; 606/167, 606/170, 181, 182, 185, 108
See application file for complete search history.

(56) References Cited

U.S. PATENT DOCUMENTS

| | | | |
|---|---|---|---|
| 3,630,192 A | 12/1971 | Jamshidi | 128/2 B |
| 4,046,144 A | 9/1977 | McFarlane | 128/214.4 |
| 4,230,123 A | 10/1980 | Hawkins, Jr. | 128/658 |
| 4,488,545 A | 12/1984 | Shen | 128/200.26 |
| RE31,855 E | 3/1985 | Osborne | 604/161 |
| 4,531,937 A | 7/1985 | Yates | 604/53 |
| 4,592,744 A | 6/1986 | Jagger et al. | 604/192 |
| 4,629,450 A | 12/1986 | Suzuki et al. | 604/164 |
| 4,747,831 A | 5/1988 | Kulli | 604/110 |
| 4,772,266 A | 9/1988 | Groshong | 604/164 |
| 4,869,366 A | 9/1989 | Bruno | 206/370 |
| 4,892,525 A | 1/1990 | Hermann et al. | 604/263 |
| 4,906,236 A | 3/1990 | Alberts et al. | 604/198 |
| 4,907,598 A | 3/1990 | Bauer | 128/753 |
| 4,909,794 A | 3/1990 | Haber et al. | 604/195 |
| 4,935,014 A | 6/1990 | Haber | 604/195 |
| 4,944,728 A | 7/1990 | Carrell et al. | 604/164 |
| 4,946,446 A | 8/1990 | Vadher | 604/198 |
| 4,966,592 A | 10/1990 | Burns et al. | 604/198 |
| 4,978,334 A | 12/1990 | Toye et al. | 604/51 |

(Continued)

FOREIGN PATENT DOCUMENTS

EP        0232994        8/1987

(Continued)

*Primary Examiner*—Cris L. Rodriguez
(74) *Attorney, Agent, or Firm*—Schwegman, Lundberg, Woessner & Kluth, P.A.

(57) ABSTRACT

An introducer assembly includes an outer sheath, and a dilator assembly that includes a dilator hub and a dilator sheath. The dilator sheath is disposed within the outer sheath passage, and a proximal end of the dilator sheath is movably disposed within the dilator hub. The dilator assembly further includes a needle disposed within the dilator sheath, and coupled with the dilator hub. The dilator sheath has a first position and a second position relative to the dilator hub, where in the first position the needle distal end extends out from the dilator sheath distal end, and in the second position the dilator sheath is extended over the needle distal end.

28 Claims, 6 Drawing Sheets

U.S. PATENT DOCUMENTS

| | | | |
|---|---|---|---|
| 4,978,344 A | 12/1990 | Dombrowski et al. | 604/198 |
| 4,994,034 A | 2/1991 | Botich et al. | 604/110 |
| 4,994,041 A | 2/1991 | Dombrowski et al. | 604/164 |
| 4,995,866 A | 2/1991 | Amplatz et al. | 604/53 |
| 4,998,921 A | 3/1991 | Vickroy et al. | 604/167 |
| 5,052,403 A | 10/1991 | Haber et al. | 128/765 |
| 5,057,083 A | 10/1991 | Gellman | 604/164 |
| 5,098,392 A | 3/1992 | Fleischhacker et al. | 604/165 |
| 5,114,404 A | 5/1992 | Paxton et al. | 604/110 |
| 5,125,414 A | 6/1992 | Dysarz | 128/763 |
| 5,129,884 A | 7/1992 | Dysarz | 604/164 |
| 5,169,387 A | 12/1992 | Kronner | 604/164.06 |
| D332,651 S | 1/1993 | Sugerman | D22/149 |
| 5,188,599 A | 2/1993 | Botich et al. | 604/110 |
| 5,190,528 A | 3/1993 | Fonger et al. | 604/171 |
| 5,193,552 A | 3/1993 | Columbus et al. | 128/760 |
| 5,195,980 A | 3/1993 | Catlin | 604/167 |
| 5,295,974 A | 3/1994 | O'Laughlin | 604/198 |
| 5,336,199 A | 8/1994 | Castillo et al. | 604/198 |
| 5,360,423 A | 11/1994 | McCormick | 604/403 |
| 5,368,574 A | 11/1994 | Antonacci et al. | 604/164 |
| 5,372,581 A | 12/1994 | Anderson | 604/32 |
| 5,389,076 A | 2/1995 | Shaw | 604/110 |
| 5,395,337 A | 3/1995 | Clemens et al. | 604/110 |
| 5,401,249 A | 3/1995 | Shields | 604/187 |
| 5,407,431 A | 4/1995 | Botich et al. | 604/110 |
| 5,409,469 A | 4/1995 | Schaerf | 604/282 |
| 5,423,758 A | 6/1995 | Shaw | 604/110 |
| 5,454,790 A | 10/1995 | Dubrul | 604/104 |
| 5,480,385 A | 1/1996 | Thorne et al. | 604/110 |
| 5,487,734 A | 1/1996 | Thorne et al. | 604/195 |
| 5,496,301 A | 3/1996 | Hlavinka et al. | 604/409 |
| 5,531,694 A | 7/1996 | Clemens et al. | 604/110 |
| 5,542,927 A | 8/1996 | Thorne et al. | 604/110 |
| 5,549,571 A | 8/1996 | Sak | 604/198 |
| 5,562,103 A | 10/1996 | Sak | 128/763 |
| 5,569,289 A * | 10/1996 | Yoon | 606/185 |
| 5,571,134 A * | 11/1996 | Yoon | 606/185 |
| 5,575,777 A | 11/1996 | Cover et al. | 604/198 |
| 5,584,848 A * | 12/1996 | Yoon | 606/185 |
| 5,607,439 A * | 3/1997 | Yoon | 606/185 |
| 5,616,135 A | 4/1997 | Thorne et al. | 604/192 |
| 5,645,556 A * | 7/1997 | Yoon | 606/185 |
| 5,669,887 A | 9/1997 | Cooper | 604/195 |
| 5,685,855 A | 11/1997 | Erskine | 604/168 |
| 5,685,863 A | 11/1997 | Botich et al. | 604/198 |
| 5,702,367 A | 12/1997 | Cover et al. | 604/110 |
| 5,709,699 A | 1/1998 | Warner | 606/181 |
| 5,741,233 A | 4/1998 | Riddle et al. | 604/165 |
| 5,755,693 A | 5/1998 | Walker et al. | 604/160 |
| 5,766,135 A | 6/1998 | Terwilliger | 600/567 |
| 5,797,880 A | 8/1998 | Erskine | 604/110 |
| 5,851,212 A | 12/1998 | Zirps et al. | 606/167 |
| 5,873,854 A | 2/1999 | Wolvek | 604/104 |
| 5,964,740 A | 10/1999 | Ouchi | 606/185 |
| 5,989,220 A | 11/1999 | Shaw et al. | 604/110 |
| 6,016,595 A | 1/2000 | Dysarz | 29/423 |
| 6,077,244 A | 6/2000 | Botich et al. | 604/110 |
| 6,096,005 A | 8/2000 | Botich et al. | 604/110 |
| 6,099,544 A * | 8/2000 | Wolf et al. | 606/185 |
| 6,102,894 A | 8/2000 | Dysarz | 604/110 |
| 6,120,494 A | 9/2000 | Jonkman | 604/506 |
| 6,156,010 A | 12/2000 | Kuracina et al. | 604/168.01 |
| 6,203,530 B1 | 3/2001 | Stewart | 604/207 |
| 6,379,337 B1 | 4/2002 | Mohammad | 604/195 |
| 6,379,338 B1 | 4/2002 | Garvin | 604/195 |
| 6,398,743 B1 | 6/2002 | Halseth et al. | 600/585 |
| 6,524,276 B1 | 2/2003 | Halseth et al. | 604/110 |
| 6,626,868 B1 | 9/2003 | Prestidge et al. | 604/158 |
| 6,641,564 B1 * | 11/2003 | Kraus | 604/164.1 |
| 2002/0045843 A1 | 4/2002 | Barker et al. | 600/585 |
| 2003/0060758 A1 | 3/2003 | Lu | 604/110 |
| 2003/0060760 A1 | 3/2003 | Botich et al. | 604/110 |
| 2003/0060772 A1 | 3/2003 | Swenson | 604/183 |

FOREIGN PATENT DOCUMENTS

| | | |
|---|---|---|
| WO | WO-98/24494 | 6/1998 |
| WO | WO-00/06221 | 2/2000 |

* cited by examiner

SAFETY INTRODUCER ASSEMBLY AND METHOD

TECHNICAL FIELD

The present application relates generally to catheters. More particularly, it pertains to catheters with safety features to prevent inadvertent needle sticks.

BACKGROUND

Introducer devices provide for access to the venous system and are employed for inserting medical devices such as catheters, guidewires, leads, infusion ports, dialysis ports, dialysis catheters, and others. A typical procedure for gaining access to a vessel using an introducer includes inserting a dilator and needle into the vessel. After the dilator and needle are removed, the sheath remains. The desired medical device is implanted through a passage of the sheath. The sheath is optionally removed from the medical device. When the needle and dilator are removed from the sheath, the needle is exposed after having been in contact with patient fluids.

Any time a needle is used it can cause transmission of various pathogens, most notably the Human Immune Virus (HIV), due to an accidental needle stick of an uninfected person after the needle is withdrawn from the patient, during disposal of the instrument, or due to re-use of a needle.

Accordingly, what is needed is an introducer and dilator which can eliminate needle re-use or inadvertent needle sticks. What is also needed is an introducer assembly which does not distract or interfere with the implantation process.

SUMMARY

An introducer assembly is provided including an outer sheath extending from an outer sheath proximal end to an outer sheath distal end, where the outer sheath includes having an outer sheath passage therein. The introducer assembly further includes a dilator assembly including a dilator hub and a dilator sheath, where the dilator sheath is disposed within the outer sheath passage. The dilator sheath proximal end is movably disposed within the dilator hub. The dilator assembly further includes a needle disposed within the dilator sheath, and coupled with the dilator hub. The dilator sheath has a first position and a second position relative to the dilator hub, where in the first position the needle distal end extends out from the dilator sheath distal end, and in the second position the dilator sheath is extended over the needle distal end. The dilator sheath is frictionally retained by the outer sheath until the dilator sheath is disposed in the second position.

Several options for the introducer assembly are as follows. For instance, in one option, the assembly further includes a catch disposed at the dilator sheath proximal end and a shoulder disposed within the dilator hub, wherein the catch is disposed against the shoulder when the dilator sheath is disposed in the second position. The catch optionally includes at least one resilient arm extending therefrom. In another option, the introducer assembly further includes a spring disposed within the dilator hub, where at least a portion of the spring is disposed between the dilator hub and the dilator sheath proximal end. In yet another option, a ring is disposed on the dilator sheath, where the ring disposed against a portion of the outer sheath when the dilator sheath is in the first position. Still further in another option, the assembly further includes at least one reset member coupled with the dilator assembly, where the reset member is, in one option, disposed in an at least partially exposed position when the dilator sheath is disposed in the second position. The at least one reset member, in another option, is disposed within the dilator hub when the dilator sheath is disposed in the first position.

In another embodiment, the introducer assembly includes an outer sheath and a dilator assembly, and at least one resilient member disposed between the dilator sheath and the dilator hub. The dilator sheath has a first position where the needle is extended out through the sheath distal end and the resilient member is at least partially compressed. The dilator sheath also has a second position wherein the dilator sheath distal end is disposed over the needle distal end.

Several options for the introducer assembly are as follows. For instance, in one option, the resilient member is less compressed when the dilator sheath is in the second position than in the first position. In another option, the assembly further includes at least one reset member coupled with the dilator assembly, where the at least reset member is optionally disposed in an at least partially exposed position when the dilator sheath is disposed in the second position.

In another embodiment, a method includes disposing a dilator assembly within an outer sheath, moving the needle toward the outer sheath proximal end; and moving the dilator sheath from the first position to the second position with a resilient member while the needle is moved toward the outer sheath proximal end.

Several options for the method are as follows. For instance, in one option, the method further includes resetting the dilator sheath to the first position, optionally including depressing a reset member and moving the dilator sheath towards the dilator hub. In another option, the method includes frictionally retaining the dilator sheath with the outer sheath while the needle is moved toward the outer sheath proximal end. In yet another option, the method further includes coupling the dilator assembly with the outer sheath while the needle is extended out from the dilator sheath. In another option, the method further includes uncoupling the dilator assembly from the outer sheath and allowing the dilator sheath to move from the first position to the second position.

In another embodiment, a method includes coupling a dilator assembly with a catheter assembly, moving a dilator hub and the needle along the longitudinal axis toward the outer sheath proximal end, frictionally retaining the dilator sheath with the outer sheath while the needle is moved toward the outer sheath proximal end, and disposing the dilator sheath distal end over the needle distal end.

Several options for the method are as follows. For instance, in one option, the method further includes resetting the dilator sheath and exposing the needle distal end after the dilator sheath distal end is disposed over the needle distal end, which optionally includes depressing a reset member and moving the dilator sheath towards the dilator hub. In another option, the method further includes coupling the dilator assembly with the outer sheath while the needle distal end extends out from the dilator sheath distal end. In yet another option, the method further includes moving the dilator sheath to a position over the needle distal end with a resilient member coupled between the dilator hub and the dilator sheath.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figures 1, 5:
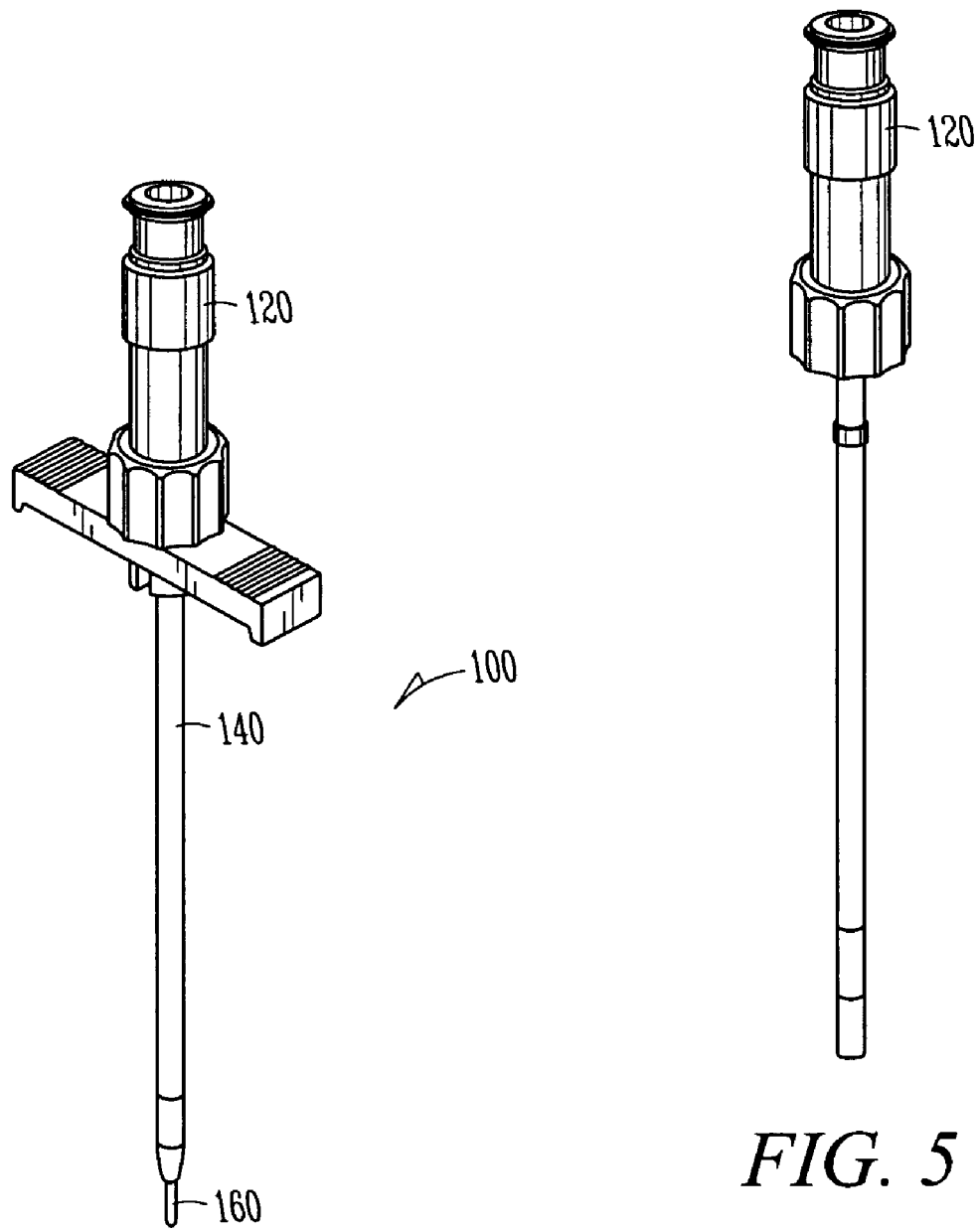
FIG. 1 is a perspective view illustrating an introducer assembly constructed in accordance with one embodiment.
FIG. 5 is a perspective view illustrating a dilator assembly constructed in accordance with one embodiment.

A safety introducer assembly 100, as shown in FIG. 1, is illustrated in its first position, where the needle, discussed further below, is not in its safetied position. The introducer assembly generally includes an outer sheath 140 and a dilator assembly 120, and a needle 160. In one option, the outer sheath 140 includes a catheter, or an introducer sheath. The dilator assembly 120 allows for the introducer assembly 100 to be introduced into a vessel of a patient, for instance, over a guidewire. Once the dilator assembly 120 is removed from the outer sheath 140, as further discussed below, the outer sheath 140 allows for additional instruments, devices, and/or fluids to be inserted therethrough and inserted into the patient.

Figure 2:
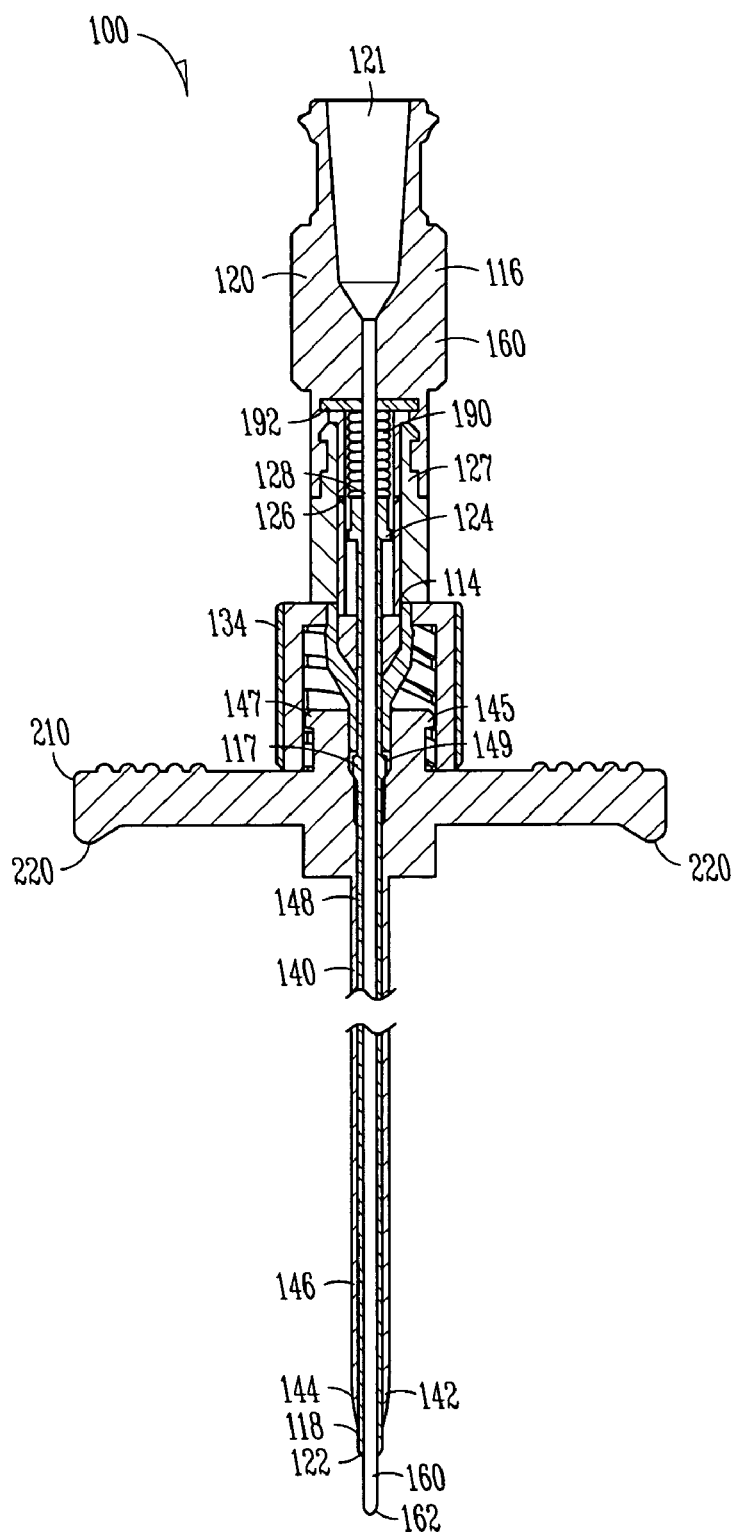
FIG. 2 is a cross-sectional view illustrating an introducer assembly constructed in accordance with one embodiment.
Figure 3:
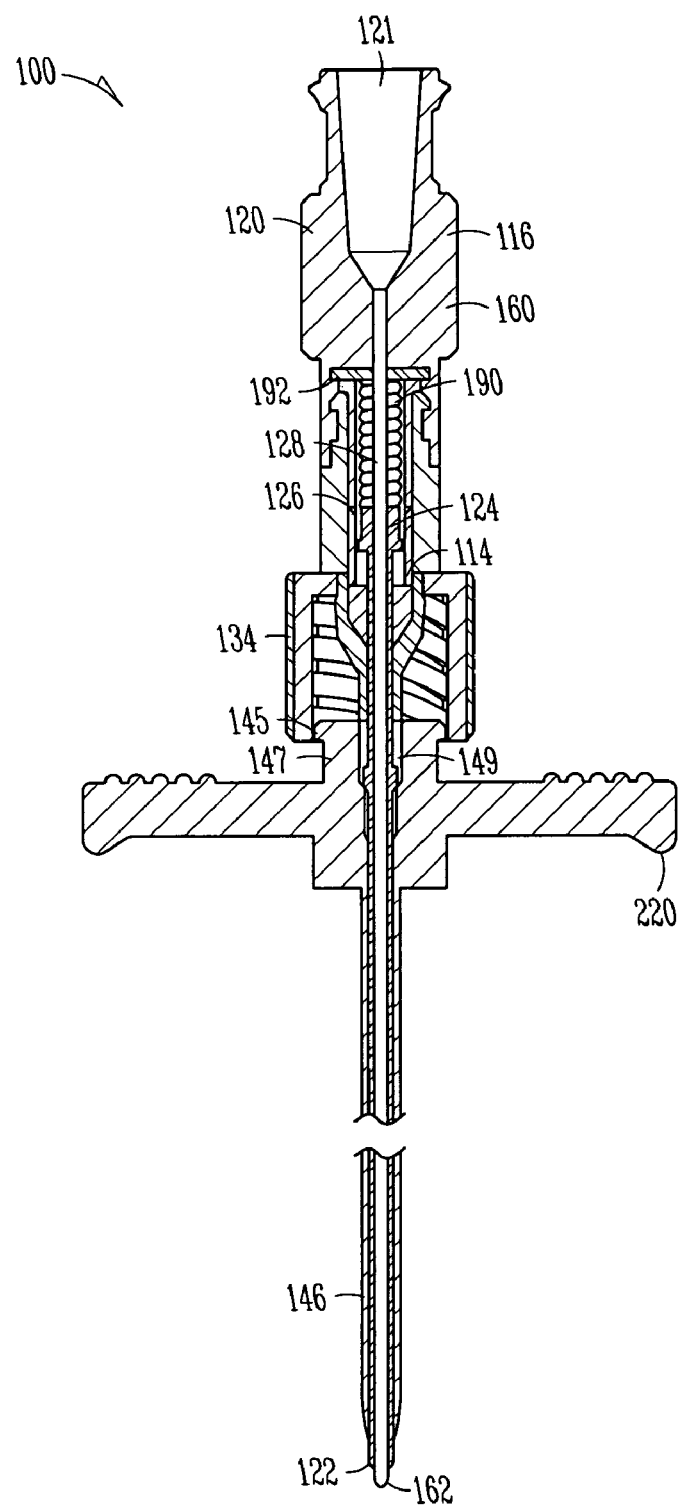
FIG. 3 is a cross-sectional view illustrating an introducer assembly constructed in accordance with one embodiment.

The outer sheath 140, is shown in greater detail in FIGS. 2 and 3, and extends from a sheath distal end 142 to a proximal end 148, where the distal end 142 is first inserted into the patient and the proximal end 148 remains outside of the patient. Near the distal end 142 is a tapered portion 144 which provides a transition to a cylindrical portion 146. The outer sheath 140 also includes a passage therethrough which allows for the introduction of the dilator assembly 120 therein. After the introducer assembly 100 has been inserted into a patient, and the dilator assembly 120 is removed, other medical devices, instruments and/or fluids can be easily inserted into and through the outer sheath 140, and introduced into the patient.

At the sheath proximal end 148, the outer sheath 140 includes at least one tab 210 which extends radially outward from the outer sheath 140. In one embodiment, the outer sheath 140 includes two tabs 220, i.e. a first tab and a second tab, which are disposed 180 degrees from each other. In another option, disposed at the sheath proximal end 148 is a sheath shoulder 149. In one option, the sheath shoulder 149 is formed as part of the passage within the outer sheath 140. In another option, the sheath proximal end 148 includes a sheath hub 147, and further optionally includes at least one outer thread 145 on the sheath hub 147.

The outer sheath 140 includes various types of sheaths, for instance, the outer sheath 140 can comprise a sheath which has a strengthening braid of material. Alternatively, the outer sheath 140 includes those which are modified to prevent bends in the outer sheath. In one option, the outer sheath is splittable or otherwise removable from around an instrument disposed therein, without damage to the instrument, for example, through use of the tabs 220. The outer sheath 140 is optionally separable or splittable which prevents disruption to or removal of instruments or devices which have been inserted through the outer sheath 140. Suitable structure to allow the outer sheath to be separable includes score lines, an external a slitting device, a rip cord or strengthening strip running along the longitudinal length of the outer sheath, a weakening which allows the introducer to be ripped apart, or other techniques. It should be noted that the above-discussed features for the outer sheath 140 are optional, and/or interchangeable.

The dilator assembly 120 includes a dilator hub 116 and a dilator sheath 118. The dilator hub 116 having a passage 121 therethrough, and a needle 160 is disposed within the passage 121. The needle 160 is mechanically coupled to the dilator hub 116. The needle 160 extends to a needle distal end 162, for example a sharpened needle distal end, which is used to pierce the outer skin on a patient, to access, for example, a vein. The needle 160 is disposed within, and extends through the dilator sheath 118.

The dilator sheath 118 is disposed within the passage of the outer sheath 140 where at least a portion of the dilator sheath 118, in one option, is at least temporarily engaged with the outer sheath 140 in an interference fit, or by friction. At least a portion of the dilator sheath 118 is movably disposed within a portion of the dilator hub 116.

The dilator sheath 118 extends from a dilator sheath distal end 122 to a dilator sheath proximal end 124, where the dilator sheath distal end 122 is insertable into a patient. The dilator sheath distal end 122 optionally ends in a tapered end. At the dilator sheath proximal end 124 is a catch 126 having a passage 128 therethrough, where the passage 128 extends through the catch 126 and the dilator sheath 118. The catch 126 moves within the dilator hub 116 from a first position (FIG. 2), through an intermediate position (FIG. 3), and to a final second position (FIG. 4), as further described below. The catch 126 is coupled with the dilator sheath 118, and so the dilator sheath 118 also moves from a first position, through an intermediate position, and to the second position. The catch 126 further includes at least one arm 127, where the arm 127 assists in preventing re-exposure of the needle 160 once it has been covered by the dilator sheath 118. The arm 127 resiliently extends from the catch 126.

The dilator sheath 118 further includes, in one option, a ring 117 projecting out from the dilator sheath 118. The ring 117 is disposed on the dilator sheath 118 between the catch 126 and the dilator sheath distal end 122. When the introducer assembly 100 is assembled and the dilator assembly 120 is coupled with the outer sheath 140, the ring 117 is disposed against the sheath shoulder 149 of the outer sheath 140, and the catch 126 of the dilator sheath 118. The ring 117 is positioned along the dilator sheath 118 such that when the ring 117 is disposed against sheath shoulder 149, and the dilator assembly 120 is coupled with the outer sheath 140, the needle 160 is exposed, and the dilator sheath 118 does not cover the needle 160, as shown in FIG. 2. It should be noted that instead of a ring 117, a projection or recess can be used, and/or the projection can be formed on the outer sheath 140. In one option, the ring 117 is frictionally engaged by the outer sheath 140.

Disposed within the dilator hub 116 is an optional resilient member 190, such as a coil spring. The coil spring is disposed between the dilator hub 116 and a portion of the dilator sheath 118, for example, the coil spring is disposed between a first shoulder 192 within the dilator hub 116 and the catch 126 of the dilator sheath 118. The resilient member 190 is compressed between the dilator hub 116 and at least a portion of the dilator sheath 118 when the dilator sheath 118 is disposed in the first position. In one option, the resilient member 190 is less compressed when the dilator sheath 118 is in the second position than in the first position.

The ring 117 of the dilator sheath 118 and the sheath shoulder 149 assist in forcing the movable dilator sheath 118 against the resilient member 190. The resilient member 190, in one option, assists in preventing re-exposure of the needle 160 once it has been covered by the dilator sheath 118. The dilator hub 116 further includes a second shoulder 114, which optionally mates with the catch 126, for instance, the at least one arm 127. The second shoulder 114, in yet another option, assists in preventing re-exposure of the needle 160 once it has been covered by the dilator sheath 118.

The dilator assembly 120 further includes a fastener which fastens the dilator assembly 120 to the outer sheath 140. In one option, the dilator assembly 120 includes rotatable fastener 134 rotatably coupled therewith. The rotatable fastener 134 allows for coupling of the dilator assembly 120 to the outer sheath 140 such that axial movement between the dilator assembly 120 and outer sheath 140 is prevented. Optionally, the rotatable fastener 134 includes an internally threaded portion which threadingly engages with the outer thread 145 of the outer sheath hub 147.

During use of the introducer assembly 100, the dilator assembly 120 is assembled with the outer sheath 140, and the fastener couples as the dilator assembly 120 with the outer sheath 140 such that axial movement between the dilator assembly 120 and the outer sheath 140 is prevented. When the dilator assembly 120 is coupled with the outer sheath 140, the needle distal end 162 is exposed, and the introducer assembly 100 is configured to be inserted into a patient. In this configuration, the introducer assembly 100 is in the first position, as shown in FIG. 2.

In this position, the ring 117 is disposed against the sheath shoulder 149, and the dilator sheath 118 does not cover the needle distal end 162. Furthermore, the catch 126 of the dilator sheath 118 compresses the resilient member 190 against the first shoulder 192 of the dilator hub 116. In the position shown in FIG. 2, the dilator sheath 118, in one option, is frictionally engaged by the outer sheath 140. Again, the introducer assembly 100 is ready to be inserted into a patient, either over a guidewire, or directly into the vein.

Once the introducer assembly 100 has been properly positioned in the patient, the dilator assembly 120 is removed so that only the outer sheath 140 is disposed within the patient. Additional instruments and/or fluids such as medication can be disposed through the outer sheath 140.

The process of removing the dilator assembly 120 from the outer sheath 140 is important, as the needle 160 is covered, and optionally prevented from further re-use during this process. In another option, as will be discussed further below, a resetting assembly is provided which allows for the dilator sheath 118 to be placed in the first position, after it has been placed in the second position.

As the dilator assembly 120 is removed from the outer sheath 140, the outer sheath 140 retains a portion of the dilator sheath 118, and the catch 126 and the dilator sheath 118 move to the intermediate position relative to the dilator hub 116, as shown in FIG. 3. In one option, the outer sheath 140 retains the dilator sheath 118 by an interference or friction fit between the ring 117 and the sheath shoulder 149. In another option, the outer sheath 140 frictionally engages a portion of the dilator sheath 118.

As the outer sheath 140 retains a portion of the dilator sheath 118 as the dilator assembly 120 is removed from the outer sheath 140, the catch 126 is effectively retained by the outer sheath 140, and the resilient member 190 becomes uncompressed by the catch 126 as the dilator assembly 120 is moved axially away from the outer sheath 140. The resilient member 190, in one option, assists in maneuvering the dilator sheath 118 to cover the needle 160, such that the dilator sheath 118 begins to move away from the dilator hub 116 and toward the needle distal end 162.

Figure 4:
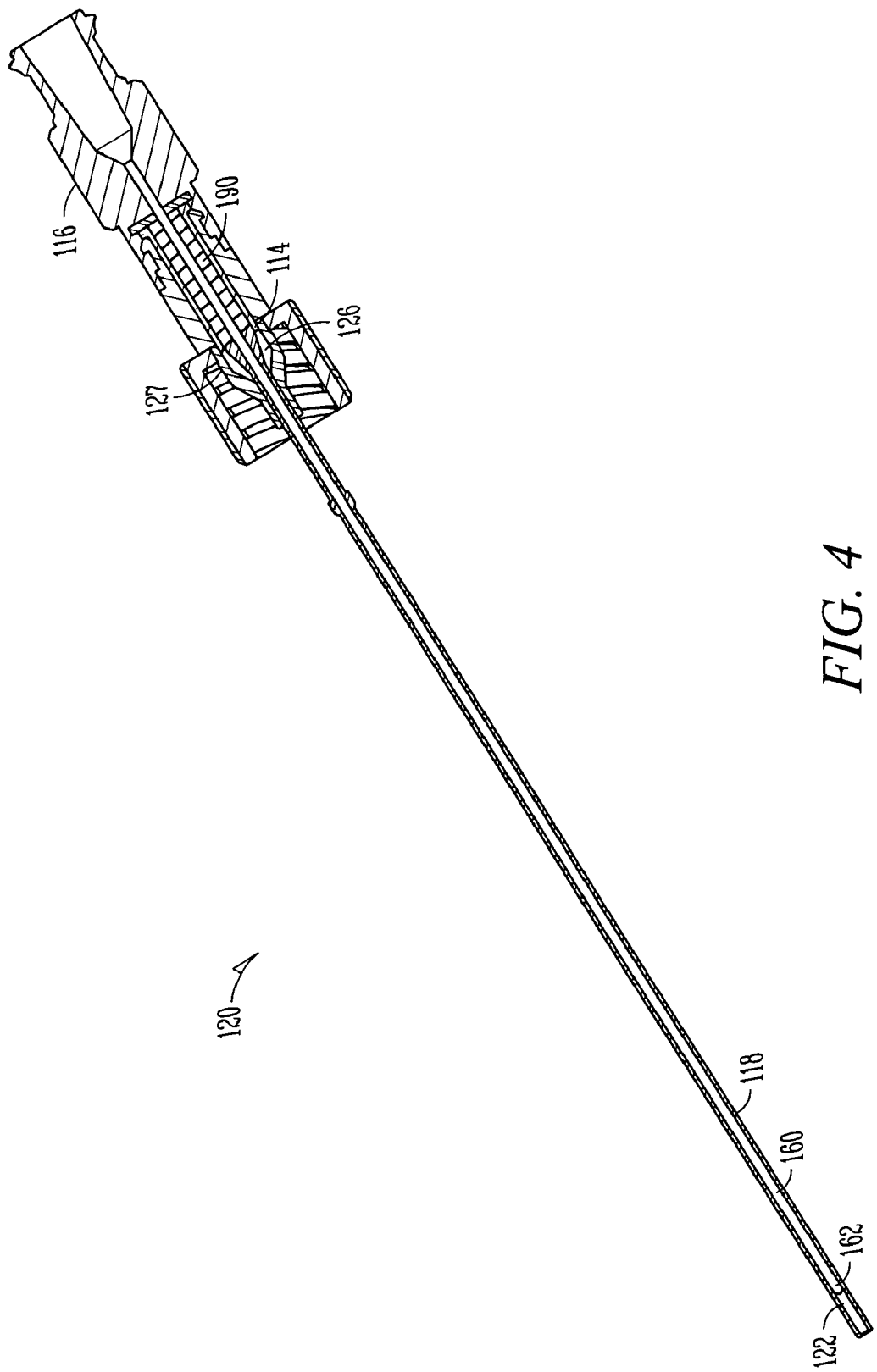
FIG. 4 is a cross-sectional view illustrating an dilator assembly constructed in accordance with one embodiment.

As the dilator assembly 120 is moved further axially away from the outer sheath 140, and the resilient member 190 becomes uncompressed, the dilator sheath distal end 122 covers the needle distal end 162 in a second position, as shown in FIG. 4. In this second position, the dilator sheath distal end 122 is disposed over the needle distal end 162, and protects the physician from sticks from a contaminated needle 160. The terms "first", "intermediate", and "second" are not intended to be limiting terms, and instead are used to indicate relatively different positions.

To move the dilator sheath 118 to the second position, the user overcomes the friction between the outer sheath 140 (FIG. 2) and the dilator sheath 118 to remove the dilator assembly 120 from the outer sheath 140 (FIG. 2). In this configuration, the dilator sheath 118 and the catch 126 have been moved relative to the dilator hub 116, and the catch 126 has been moved axially past the second shoulder 114 of the dilator hub 116. At least one arm 127 expands, and catches the second shoulder 114, such that the dilator sheath 118 cannot be moved back toward the dilator hub 116, and the needle 160 cannot be re-exposed. In another option, the resilient member 190 assists in preventing the dilator sheath 118 from movement back toward the dilator hub 116, and the needle 160 cannot be re-exposed. It should be noted that any combination of these can also be used to prevent re-exposure of the needle 160. In this second position, the needle 160 has been safely covered by the dilator sheath 118, and can be safely disposed of.

Figure 6:
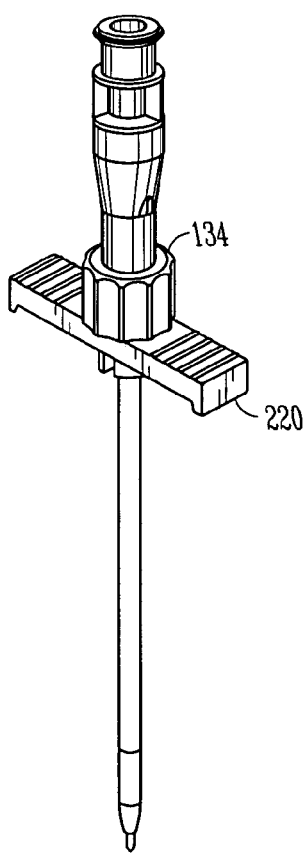
FIG. 6 is a perspective view illustrating an introducer assembly constructed in accordance with one embodiment.
Figure 7:
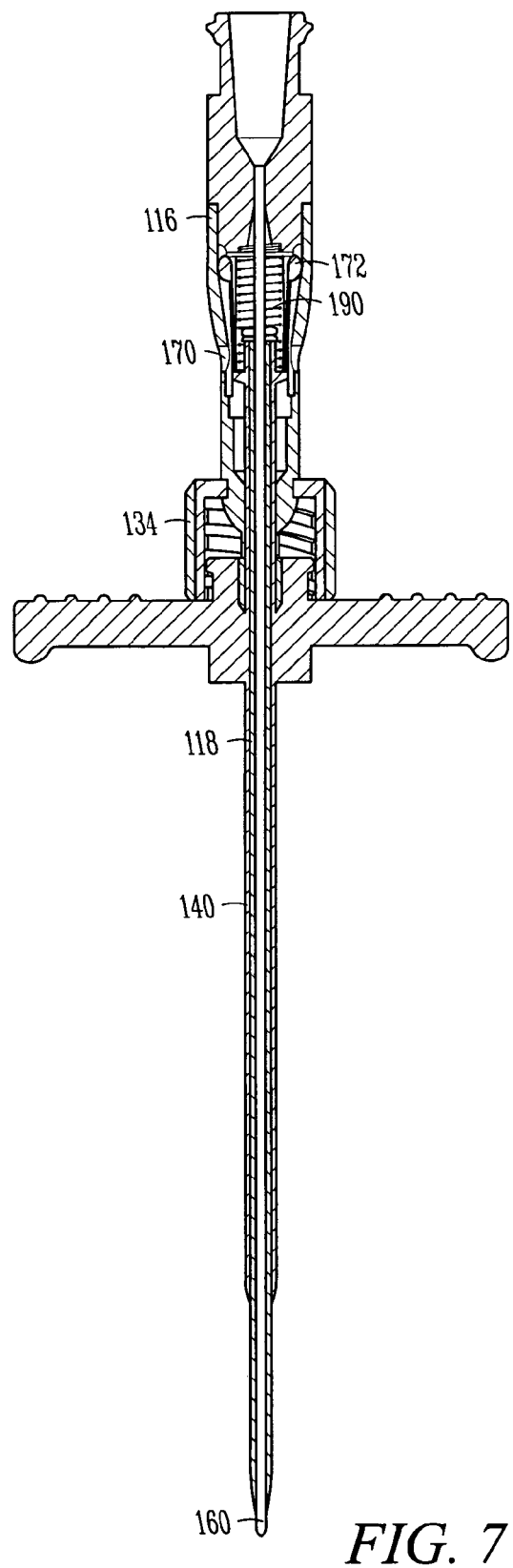
FIG. 7 is a cross-sectional view illustrating an introducer assembly constructed in accordance with one embodiment.
Figure 8:
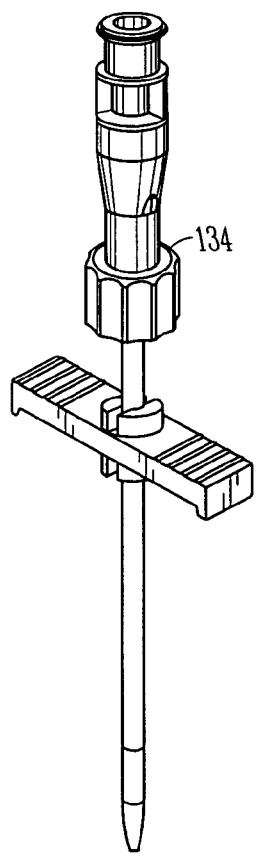
FIG. 8 is a perspective view illustrating an introducer assembly constructed in accordance with one embodiment.
Figure 9:
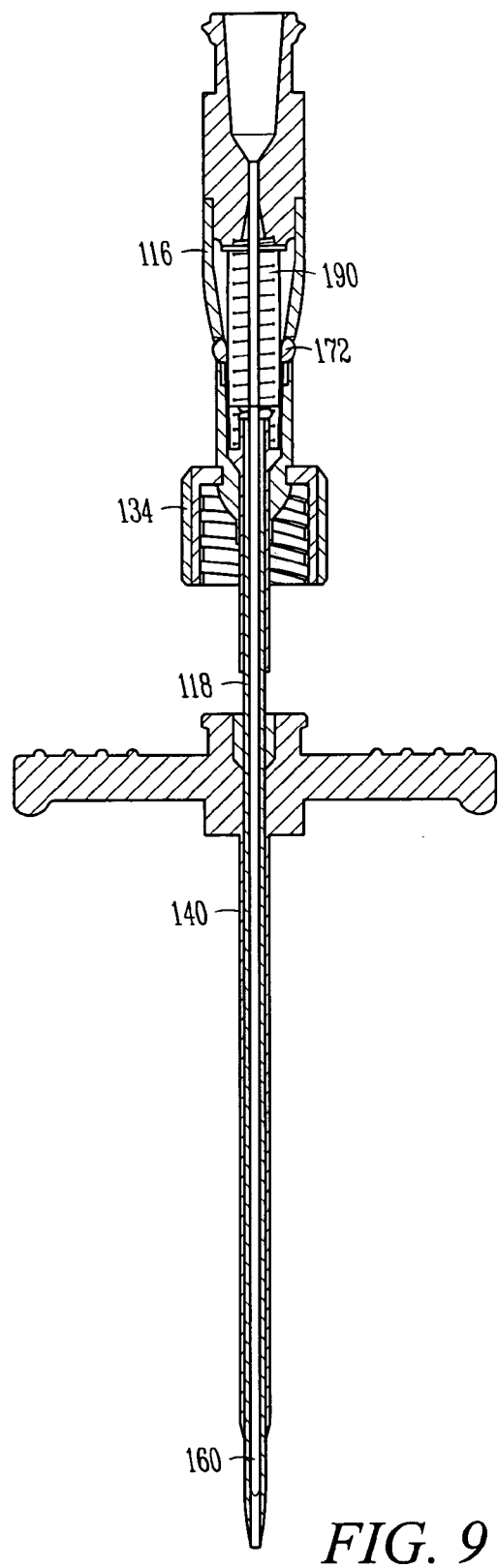
FIG. 9 is a cross-sectional view illustrating an introducer assembly constructed in accordance with one embodiment.

FIGS. 6–9 illustrate another embodiment, which incorporates all of the above-discussed embodiments. Referring to FIGS. 6 and 7, the dilator sheath 118 is disposed in the first position where the needle 160 is exposed, as discussed above. The dilator assembly 120 includes at least one reset assembly. The assembly includes at least one reset member 172 coupled with the dilator sheath 118. The reset assembly allows for the dilator sheath 118 to be positioned back to the first position, after the dilator sheath 118 has been moved to the second position (FIGS. 8 and 9). When the dilator sheath 118 is disposed in the first position and the needle 160 is exposed as shown in FIGS. 6 and 7, the at least one reset member 172 is disposed with the dilator hub 116, or is otherwise contained or covered.

Referring to FIGS. 8 and 9, the dilator sheath 118 is placed in the second position, covering the needle 160, as discussed in the various embodiments above. In this position, the at least one reset member 172 is at least partially exposed through an opening 170 in the dilator hub 116, as shown in FIGS. 8 and 9. To move the dilator sheath 118 back to the first position where the needle 160 is exposed, the physician depresses the at least one reset member 172 to a position within the dilator hub 116, and the physician moves the dilator sheath 118 toward the dilator hub 116, and re-couples the dilator assembly 120 with the outer sheath 140 to expose the needle 160.

Advantageously, the introducer assembly allows for the medical technician or physician to remove the dilator assembly from the outer sheath and automatically placing the needle in a safety position. This improves the implanting process and reduces risk to the physician. In addition, the medical technician or physician will not become distracted by inadvertently sticking themselves with a needle that has been in contact with patient fluid.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g. "Such as") provided herein, is intended merely to better illuminate the invention and does not pose a limitation on the scope of the invention unless otherwise claimed. No language in the specification should be construed as indicating any non-claimed element as essential to the practice of the invention.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An introducer assembly comprising:
an outer sheath extending from an outer sheath proximal end to an outer sheath distal end, the outer sheath having an outer sheath passage therethrough;
a dilator assembly including a dilator hub and a dilator sheath, the dilator sheath disposed within the outer sheath passage, the dilator sheath extending from a dilator sheath proximal end to a dilator sheath distal end, the dilator sheath proximal end movably disposed within the dilator hub;
the dilator assembly including a needle disposed within the dilator sheath, the needle extending from a needle proximal end to a needle distal end, the needle proximal end coupled with the dilator hub;
the dilator sheath having a first position and a second position relative to the dilator hub, in the first position the needle distal end extends out from the dilator sheath distal end, in the second position the dilator sheath is extended over the needle distal end; and
the dilator sheath frictionally retained by the outer sheath until the dilator sheath is disposed in the second position.

2. The introducer assembly as recited in claim 1, further comprising a catch disposed at the dilator sheath proximal end and a shoulder disposed within the dilator hub, wherein the catch is disposed against the shoulder when the dilator sheath is disposed in the second position.

3. The introducer assembly as recited in claim 2, wherein the catch further comprises at least one resilient arm extending therefrom.

4. The introducer assembly as recited in claim 1, further comprising a spring disposed within the dilator hub, where at least a portion of the spring is disposed between the dilator hub and the dilator sheath proximal end.

5. The introducer assembly as recited in claim 1, further comprising a ring disposed on the dilator sheath, the ring disposed against a portion of the outer sheath when the dilator sheath is in the first position.

6. The introducer assembly as recited in claim 1, further comprising at least one reset member coupled with the dilator assembly.

7. The introducer assembly as recited in claim 6, wherein the at least one reset member is disposed in an at least partially exposed position when the dilator sheath is disposed in the second position.

8. The introducer assembly as recited in claim 6, wherein the at least one reset member is disposed within the dilator hub when the dilator sheath is disposed in the first position.

9. An introducer assembly comprising:
an outer sheath extending from an outer sheath proximal end to an outer sheath distal end, the outer sheath having a sheath passage therethrough;
a dilator assembly including a dilator hub and a dilator sheath, at least a portion of the dilator sheath movably disposed within the dilator hub, the dilator sheath having a dilator sheath proximal end and a dilator sheath distal end;
the dilator assembly including a needle disposed within the dilator sheath, the needle extending from a needle proximal end to a needle distal end;
at least one resilient member disposed between the dilator sheath and the dilator hub;
the dilator sheath having a first position and a second position, in the first position the needle is extended out through the sheath distal end and the resilient member is at least partially compressed, in the second position the dilator sheath distal end is disposed over the needle distal end; and
wherein the dilator assembly is coupled with the outer sheath when the dilator sheath is in the first position, and the dilator assembly is not coupled with the outer sheath when the dilator sheath is in the second position.

10. The introducer assembly as recited in claim 9, wherein the resilient member is less compressed when the dilator sheath is in the second position than in the first position.

11. The introducer assembly as recited in claim 9, further comprising at least one reset member coupled with the dilator assembly.

12. The introducer assembly as recited in claim 11, wherein the at least one reset member is disposed in an at least partially exposed position when the dilator sheath is disposed in the second position.

13. The introducer assembly as recited in claim 11, wherein the at least one reset member is disposed within the dilator hub when the dilator sheath is disposed in the first position.

14. The introducer assembly as recited in claim 9, further comprising means for preventing re-exposure of the needle after the sheath is placed in the second position.

15. The introducer assembly as recited in claim 9, wherein the dilator sheath is retained by the outer sheath in a friction fit when the sheath is disposed in the first position.

16. The introducer assembly as recited in claim 1, wherein the dilator assembly is coupled with the outer sheath when the dilator sheath is in the first position, and the dilator assembly is not coupled with the outer sheath when the dilator sheath is in the second position.

17. An introducer assembly comprising:
an outer sheath extending from an outer sheath proximal end to an outer sheath distal end, the outer sheath having a sheath passage therethrough;
a dilator assembly including a dilator hub and a dilator sheath, at least a portion of the dilator sheath movably disposed within the dilator hub, the dilator sheath having a dilator sheath proximal end and a dilator sheath distal end;
the dilator assembly including a needle disposed within the dilator sheath, the needle extending from a needle proximal end to a needle distal end;
at least one resilient member disposed between the dilator sheath and the dilator hub;
the dilator sheath having a first position and a second position, in the first position the needle is extended out through the sheath distal end and the resilient member is at least partially compressed, in the second position the dilator sheath distal end is disposed over the needle distal end; and
wherein moving the dilator assembly axially away from the outer sheath moves the dilator sheath from first position to the second position.

18. A method comprising:
disposing a dilator assembly within an outer sheath, the outer sheath extending from an outer sheath proximal end to an outer sheath distal end, the outer sheath having a sheath passage therethrough, the dilator assembly including a dilator hub and a dilator sheath, the dilator movably disposed within the dilator hub, the dilator assembly including a needle disposed within the dilator sheath, the needle extending from a needle proximal end to a needle distal end, at least one resilient member disposed between the dilator sheath and the dilator hub, the dilator sheath having a first position and a second position, in the first position the needle is extended out through the sheath distal end and the resilient member is at least partially compressed, in the second position the dilator sheath distal end is disposed over the needle distal end;
moving the needle toward the outer sheath proximal end; and
moving the dilator sheath from the first position to the second position with the resilient member while the needle is moved toward the outer sheath proximal end; and
coupling the dilator assembly with the outer sheath while the dilator sheath is disposed in the first position.

19. The method as recited in claim 18, further comprising resetting the dilator sheath to the first position.

20. The method as recited in claim 19, wherein resetting the dilator sheath to the first position includes depressing a reset member and moving the dilator sheath towards the dilator hub.

21. The method as recited in claim 18, further comprising frictionally retaining the dilator sheath with the outer sheath while the needle is moved toward the outer sheath proximal end.

22. The method as recited in claim 18, further comprising uncoupling the dilator assembly from the outer sheath and allowing the dilator sheath to move from the first position to the second position.

23. A method comprising:
coupling a dilator assembly with a catheter assembly, the catheter assembly including an outer sheath extending from an outer sheath proximal end to an outer sheath distal end, the outer sheath having an outer sheath passage therethrough; the dilator assembly including a dilator hub and a dilator sheath, the dilator sheath disposed within the outer sheath passage, the dilator sheath extending from a dilator sheath proximal end to a dilator sheath distal end, the dilator sheath proximal end movably disposed within the dilator hub; the dilator assembly including a needle disposed within the dilator sheath, the needle extending from a needle proximal end to a needle distal end, the needle proximal end coupled with the dilator hub;
moving the dilator hub and the needle along the longitudinal axis toward the outer sheath proximal end;
frictionally retaining the dilator sheath with the outer sheath while the needle is moved toward the outer sheath proximal end;
disposing the dilator sheath distal end over the needle distal end.

24. The method as recited in claim 23, further comprising resetting the dilator sheath and exposing the needle distal end after the dilator sheath distal end is disposed over the needle distal end.

25. The method as recited in claim 24, wherein resetting the dilator sheath includes depressing a reset member and moving the dilator sheath towards the dilator hub.

26. The method as recited in claim 23, further comprising coupling the dilator assembly with the outer sheath while the needle distal end extends out from the dilator sheath distal end.

27. The method as recited in claim 23, further comprising moving the dilator sheath to a position over the needle distal end with a resilient member coupled between the dilator hub and the dilator sheath.

28. The method as recited in claim 23, further comprising uncoupling the dilator assembly from the outer sheath and allowing the dilator sheath to move from the first position to the second position.

* * * * *